United States Patent [19]

Bücheler et al.

[11] Patent Number: 5,116,536

[45] Date of Patent: * May 26, 1992

[54] PREPARATION OF PHARMACEUTICAL OR COSMETIC DISPERSIONS

[75] Inventors: Manfred Bücheler, Overath; Hans Gehringer, Cologne; Bernd Klinksiek; Bernd Koglin, both of Bergisch Gladbach, all of Fed. Rep. of Germany

[73] Assignee: Bayer Aktiengesellschaft, Leverkusen, Fed. Rep. of Germany

[*] Notice: The portion of the term of this patent subsequent to Feb. 26, 2008 has been disclaimed.

[21] Appl. No.: 581,867

[22] Filed: Sep. 13, 1990

Related U.S. Application Data

[63] Continuation of Ser. No. 07/324,985, Mar. 15, 1989, Pat. No. 4,996,004, which is a continuation of Ser. No. 518,902, Aug. 1, 1983, abandoned.

[30] Foreign Application Priority Data

Aug. 14, 1982 [DE] Fed. Rep. of Germany ....... 3230289

[51] Int. Cl.$^5$ .............................................. B01J 13/00
[52] U.S. Cl. ................................. 252/314; 252/309; 252/312; 366/340; 424/59; 514/941; 514/942; 514/943
[58] Field of Search ............... 252/312, 314; 514/941, 514/942, 943

[56] References Cited

U.S. PATENT DOCUMENTS

| | | | |
|---|---|---|---|
| 1,496,858 | 6/1924 | Knollenberg | 252/314 |
| 1,707,466 | 4/1929 | Volck | 252/312 X |
| 2,254,049 | 8/1941 | Schutte | 252/314 |
| 2,524,590 | 10/1950 | Boe | 252/305 |
| 2,665,206 | 1/1954 | Bradley | 252/312 X |
| 2,803,565 | 8/1957 | Sagar | 252/312 X |
| 3,137,623 | 6/1964 | Gessler | 514/179 |
| 3,954,658 | 5/1976 | Tsutsumi et al. | 252/312 |
| 4,996,004 | 2/1991 | Bücheler et al. | 252/314 |

FOREIGN PATENT DOCUMENTS 764918 1/1957 United Kingdom ............. 252/314

OTHER PUBLICATIONS

CRC Handbook of Chemistry and Physics, 62nd Edition, 1981–1982, Weast and Astle, pp. F-115, F-116 and F-119.

Primary Examiner—Richard D. Lovering
Attorney, Agent, or Firm—Sprung, Horn, Kramer & Woods

[57] ABSTRACT

The invention relates to a process for the preparation of fine-particled, stable, pharmaceutical or cosmetic dispersions consisting of an aqueous phase and an organic phase which is insoluble or not completely soluble in water (oily phase), in which a pre-emulsion is first prepared from the two phases by known emulsifying methods and is then further processed to the end product. The invention furthermore relates to apparatus for carrying out the process.

3 Claims, 2 Drawing Sheets

PREPARATION OF PHARMACEUTICAL OR COSMETIC DISPERSIONS

This is a continuation of application Ser. No. 324,985, filed Mar. 15, 1989 now U.S. Pat. No. 4,996,004 which is a continuation of application Ser. No. 518,902 filed Aug. 1, 1983 now abandoned.

The invention relates to a process for the preparation of fine-particled, stable, pharmaceutical or cosmetic dispersions consisting of an aqueous phase and an organic phase which is insoluble or not completely soluble in water (oily phase), in which a pre-emulsion is first prepared from the two phases by known emulsifying methods and is then further processed to the end product. The invention furthermore relates to apparatus for carrying out the process.

Pharmaceutical or cosmetic emulsions are usually prepared by combining, at a temperature of 60° to 80° C., the molten organic phase (oily phase) and the entire aqueous phase, which has been brought to the same temperature, in a stirred kettle and, in the case of ointments and creams, cooling the mixture to room temperature in an ointment reactor with stirring and homogenising tools and thereby homogenising it. In the case of emulsions which are capable of flowing, the crude emulsion thus obtained is pre-emulsified, cooled to 20° to 40° C. in a jacketed or flow-through cooler and then very finely dispersed with a high-pressure homogeniser. A disadvantage in this type of preparation of an emulsion which is capable of flowing is that the entire batch must first be heated up and then cooled again, after pre-emulsification, in order to bring the entire emulsion to the desired fineness with frequently only a small amount of disperse oily phase by means of high-pressure homogenisers. High-pressure homogenisers require a very high operating pressure in the order of size of 200 bar, which can only be produced with relatively expensive multistage high-pressure piston pumps of high power. Moreover, the temperature programme described above, necessitated by the technology, gives rise to a high energy consumption.

A further disadvantage is that high-molecular organic compounds may be destroyed by the high shearing forces in the high-pressure homogeniser, so that damage to the product occurs.

Expensive ointment reactors (heavy machine columns, vacuum devices, complicated shaft packing and the like) in which completely undefined preparation conditions prevail as a result of simultaneous stirring, homogenising and cooling (for example each volume element of the product will pass through the shearing gap of the homogeniser only on a statistical average basis) have hitherto been used for the preparation of ointment and cream products. Moreover, poor heat transfer gives rise to long cooling times.

The invention is based on the object of improving the economics of the known processes. This is to be understood as meaning that the aim is also an advantageous energy balance, together with the least possible expenditure on apparatus (reduction of the capital and operating costs). As a peripheral condition, it should be ensured that no damage occurs to the product (shearing forces too high) and that the properties of the particles (average particle size and particle size distribution) are the same as in the known processes.

According to the invention, this object is achieved, starting from the process described above, by a process in which the pre-emulsion prepared by known emulsifying methods is passed to a jet disperser in which homogenisation and fine dispersion characteristic for the end product is carried out. "Jet disperser" here is understood as meaning a pressure release jet in which the pressure energy available is dissipated in a dispersing zone in the smallest possible volume and a high dispersing efficiency, based on the volume, is achieved.

The process according to the invention is advantageously combined with a phase inversion process. In the phase inversion process, to prepare the pre-emulsion, the oily phase is first taken, as the external phase, and the aqueous phase is emulsified therein, as the internal phase. Thus, in contrast to the end product, the aqueous phase forms the internal (disperse) phase and the oily phase forms the external (continuous) phase in the pre-emulsion. The pre-emulsion thus prepared is then pumped through the jet disperser in the subsequent process step, the temperature, proportions of the two phases and pressure in the jet disperser being adjusted so that phase inversion of the emulsion takes place in the jet disperser at the same time as homogenisation and fine dispersion. On passing through the jet disperser, the aqueous phase is thus converted into the external phase and the oily phase is converted into the internal phase. The phase inversion temperature appropriate for certain proportions can be determined empirically without problems.

Use of the phase inversion process in combination with the jet disperser leads to a very simple dispersing process. For example, if, for homogenisation by the standard technique, a homogenising pressure of 200 bar were required using a high-pressure homogeniser and 40 to 50 bar were required using a jet disperser, an operating pressure in the range of only 2 to 50 bar, preferably 10 to 50 bar, which can be produced even with relatively simple and inexpensive pumps, is sufficient for the combination of jet dispersion and the phase inversion process.

A preferred embodiment of the invention comprises carrying out the phase inversion at a concentration of 50 to 70% by weight of oily phase (corresponding to 50 to 30% by weight of aqueous phase). This means that a highly concentrated emulsion is obtained on jet dispersion and is later diluted to the desired end concentration. Dilution is effected by adding cold aqueous phase, so that cooling takes place at the same time. Since the process has to be carried out with only a fraction of the total amount of emulsion, a high space/time yield is achieved, together with an advantageous energy balance. This means that it is possible to prepare either the same amount, in comparison with the processes used earlier, with a smaller kettle Volume, or a considerably greater amount of product, with a correspondingly enlarged diluter kettle capacity, in one batch. Cosmetic and pharmaceutical dispersions (see examples 1 to 4) are generally composed of the following base components:

1. The aqueous phase consists of an aqueous solution of glycerol, glycol, cosmetic or pharmaceutical active compounds, additives which increase the viscosity and preservatives.

2. The organic oily phase which is insoluble or not completely soluble in water consists of glycerol esters or fatty acid esters and/or liquid or semi-solid hydrocarbons, polyhydric alcohols, non-ionic emulsifiers and fat-soluble pharmaceutical or cosmetic active compounds.

In the pre-emulsion, the aqueous phase forms the internal phase and the oily phase the external phase, whilst in the finished end product the oily phase is finely dispersed as an internal phase in the aqueous phase.

The process according to the invention is carried out with two emulsifying apparatuses connected in series. The second emulsifying apparatus is a jet disperser, which operates under technologically optimum conditions. It consists of one or more jets, which are designed as capillary bores with a diameter of 0.3 to 1 mm, preferably 0.5 to 0.8 mm, and have a length to diameter ratio of 1 to 4, preferably of 1.5 to 2. With these dimensions, the volume of the dispersing zone is only 0.1 $mm^3$ to 1 $mm^3$. It has been found that almost all the pump energy is used up in the dispersing zone and the dispersion leaves the dispersing zone as a non-directional stream.

The jets are arranged either so that the issuing stream of emulsion hits a solid wall or the streams of emulsion collide with one another. In the latter embodiment, the kinetic energies still present after the streams have issued from the jets are used up by the streams colliding.

The essential and surprising advantage of the process according to the invention is that an improved space/time yield is achieved with a simplified apparatus. The fact that the same particle fineness as with the high-pressure homogenisers used earlier can be achieved with the jet disperser even with a substantially lower pressure and as a result less expensive pumps is of importance. Moreover, the process is not harmful to the product, since the high-molecular constituents in the oily phase and the aqueous phase are exposed to lower shearing forces in the jet disperser. In contrast to earlier processes, the energetic process conditions are strictly defined in the preparation of ointments and creams. The pre-emulsion completely is forced to flow through a dispersion zone of uniform energy dissipation density. In particular, a very narrow particle size distribution spectrum is produced in the jet disperser. Transfer of the model from the laboratory scale to the production scale is thus entirely without problems. In the text which follows, the invention is described in more detail with the aid of embodiment examples and drawings. In the figures:

Figure 1:
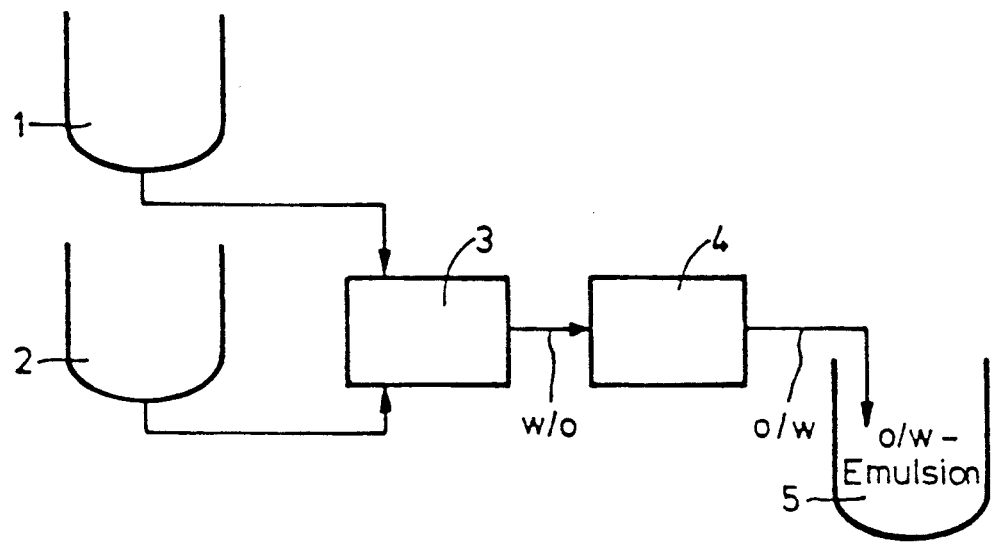
FIG. 1 shows a flow chart for the process according to the invention.

According to FIG. 1, the aqueous phase is in a kettle 1 and the oily phase is in a kettle 2. If necessary, the kettle temperatures must be adjusted by heating so that the temperature of the two phases is above the solidification point of any solid constituents present. The two phases are then stirred together in the stirred kettle 3 and pre-emulsified. The pre-emulsion thus prepared is then pumped out of the stirred kettle 3 through the jet disperser 4, in which the homogenisation and fine dispersion characteristic of the end product is effected. Thereafter, the highly concentrated emulsion is adjusted to the desired end concentration by passing the aqueous phase into the storage kettle 5 (Dilution).

The process, which is carried out discontinuously here, can also be carried out by a continuous procedure. In this case, both phases are continuously metered from kettles 1 and 2 into stirred kettle 3, pre-emulsified and then pumped through the jet disperser 4.

In many cases, it is easier to produce a water-in-oil emulsion of high particle fineness than an oil-in-water emulsion. In such cases, the process described above is modified in that phase inversion occurs in the jet disperser 4. The procedure here is to initially introduce the oil phase from kettle 2 into the stirred kettle 3 and then slowly to mix in the aqueous phase. A pre-emulsion in which the oil phase forms the external phase and the aqueous phase forms the internal phase is thereby formed (W/O emulsion). On subsequent dispersion and homogenisation in the jet disperser 4, phase inversion then takes place in a manner such that the external phase becomes the internal phase and the internal phase becomes the external phase. An oil-in-water emulsion (O/W emulsion) is formed. The concentrations of the two phases (proportions), the temperature and the mechanical stress in the jet disperser 4 are decisive for the phase inversion point. The phase inversion point for a given product can be determined empirically, without problems, as a function of the abovementioned process parameters. Furthermore, physical measurement methods, such as, for example, measurement of the electrical conductivity or ultrasonic absorption, can be used to determine the phase inversion point, since these parameters change drastically at the phase inversion point.

Figure 2:
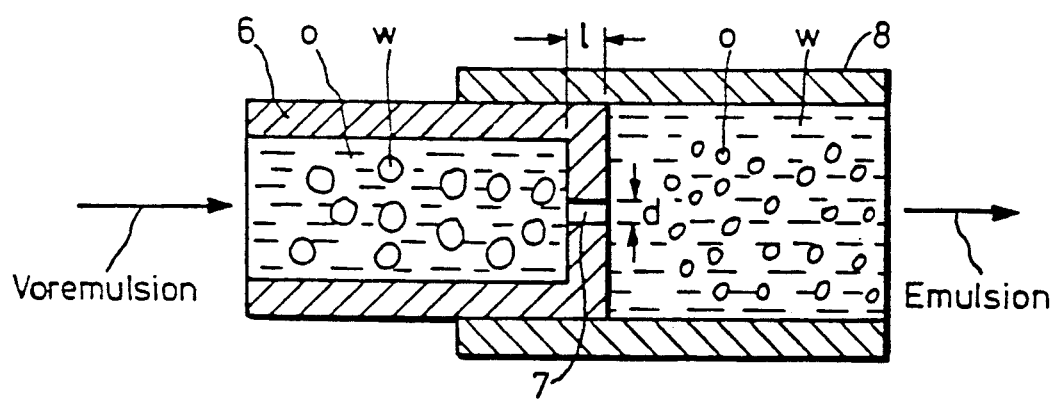
FIG. 2 shows an embodiment of the jet disperser in which the pre-emulsion passes directly from a capillary bore in the sealed end of the feed tube into an outflow tube tightly connected to the feed tube.

Various technical embodiments of the jet disperser 4 are described in the following text. The simplest embodiment of a jet disperser is shown in FIG. 2. It consists of a feed tube 6, the end of which is closed except for a capillary bore 7, and the tube is connected to an outflow tube 8 through this capillary bore. Moreover, the outflow tube 8 is connected tightly to the feed tube 6. The diameter d of the capillary bore is, for example, 0.6 mm, and its length l is 1 mm. Systematic series of experiments have shown that optimum results in respect of particle properties and energy dissipation are obtained if the following dimensions are maintained:

0,3 mm $\leq d \leq$ 1 mm 1,5 $\leq l/d \leq$ 2

Figure 3:
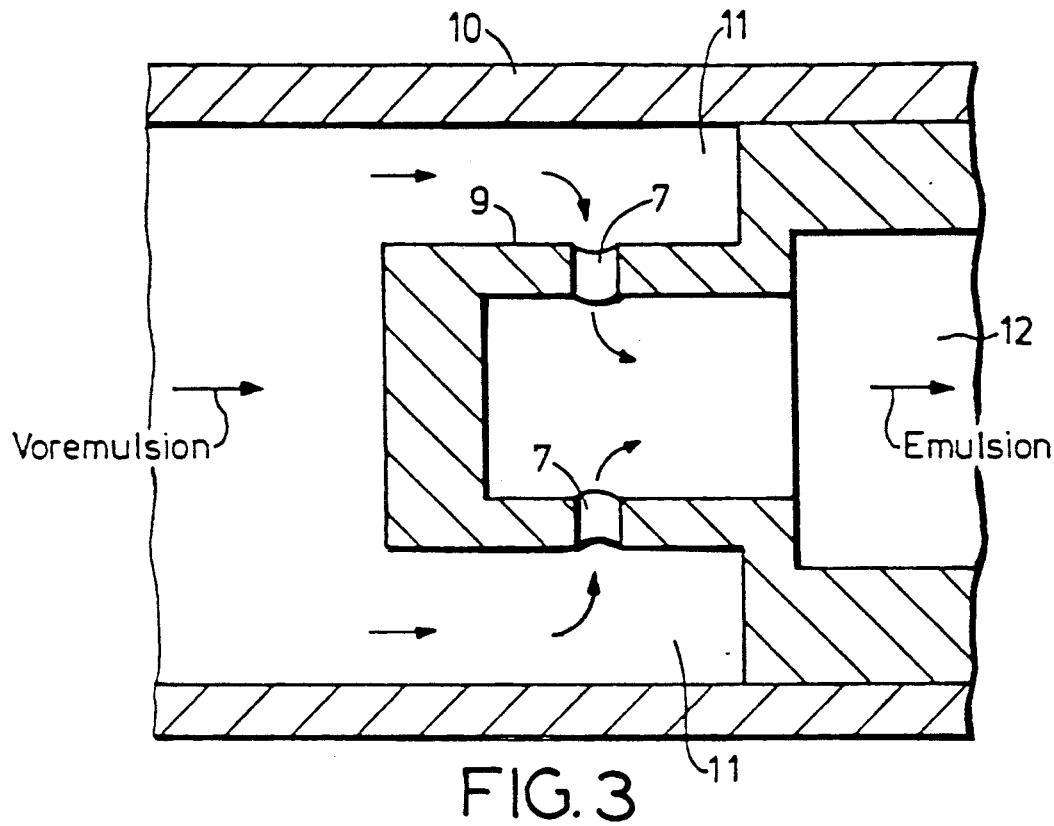
FIG. 3 shows an embodiment of the jet disperser in which the pre-emulsion flows through an annular space between a relatively large diameter feed tube and relatively small diameter tubular piece open on one end and having capillary bores opposite one another so that opposed jets of emulsion collide with each other in the tubular piece.
Figure 4:
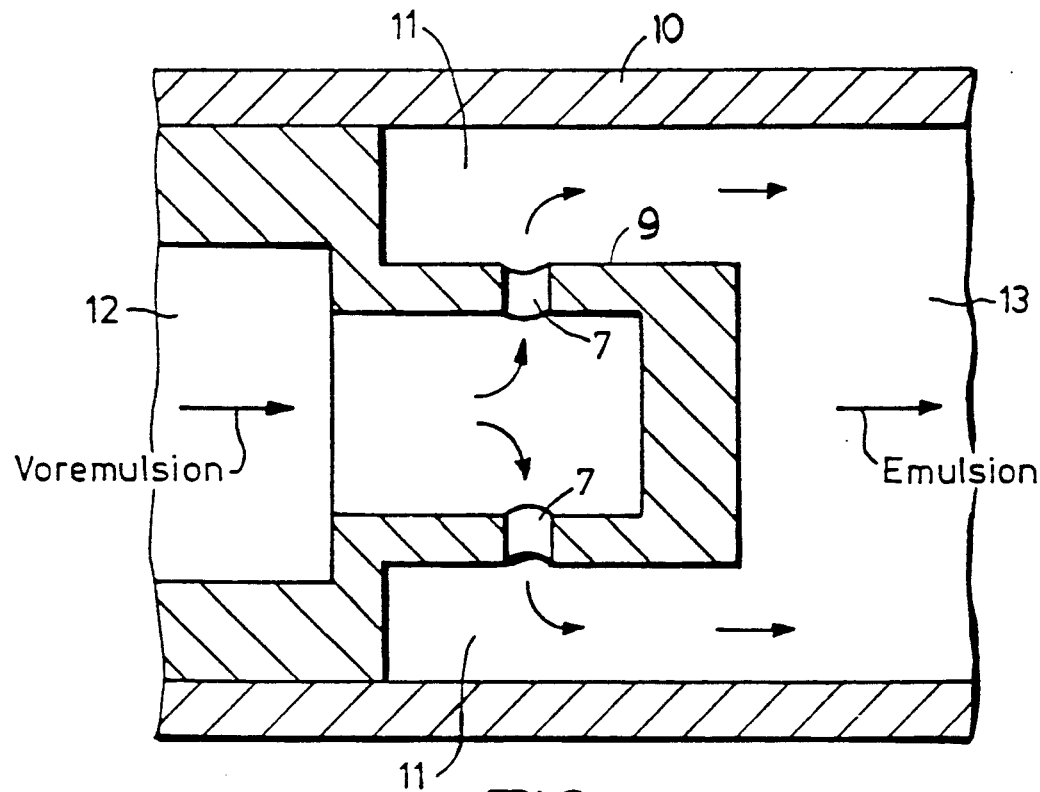
FIG. 4 shows an embodiment of the jet disperser in which the pre-emulsion flows through opposed jets in a relatively small diameter inner tube into the annular space between a relatively large diameter external tube and the inner tube, and the steams of emulsion issuing from said jets hit the internal wall of the external tube.

An alternative embodiment of the jet disperser is shown schematically in FIGS. 3 and 4. In this embodiment, a tubular piece 9, open on one side and having a relatively small diameter is inserted in a tube 10, which is also open on one side, having a relatively large diameter. An annular space 11 remains between the internal wall of the external tube 10 and the external wall of the tubular piece 9. In the region of this annular space, the tubular piece 9 is provided with capillary bores 7 opposite one another. As is similarly the case in the embodiment according to FIG. 2, these capillary bores form the only connection between the tubes 10 and 9. According to FIG. 3, the pre-emulsion flows through the tube 10 into the annular space 11, and from there through the capillary bores into the tubular piece 9.

Since the jets 7 are opposite one another, the issuing streams of emulsion collide with one another in tube 9. A particularly good dispersion is thereby achieved. The homogenised emulsion leaves the jet disperser through the outflow 12.

The apparatus of the jet disperser according to FIG. 4 is identical to that of the disperser according to FIG. 3. However, from the point of view of flow, it is operated in the reverse direction. In this case, the pre-emulsion is fed through the opening 12 of the inner tube 9 and then flows through the jets 7, which are opposite one another, into the annular space 11 between the internal tube 9 and the external tube 10. The streams of emulsion issuing from the jets 7 hit the internal wall of the tube 10 and flow from there to the drainage opening 13. The internal wall of the tube 10 is thus a baffle for the streams of emulsion. In the embodiment according to FIG. 4, tube 9 is the feed tube and tube 10 is the drainage tube of the jet disperser. In contrast, in the embodiment according to FIG. 3, tube 10 is to be regarded as the feed tube and tube 9 as the drainage tube. The jets or capillary bores 7 are located, uniformly distributed over the circumference, such that their axes intersect at a point on the longitudinal axis of the jet disperser. The above specification applies in respect of their dimensions.

The apparatuses of the jet dispersers described here are of very simple and compact construction and can therefore be produced inexpensively in any workshop. A pressure of the order of magnitude of 10 to 50 bar is required for their operation. This pressure is substantially lower than the pressure required for operating a highpressure homogeniser. For this reason, simple feed pumps, such as, for example, geared pumps or single-stage or multi-stage eccentric screw pumps, are completely adequate. Instead of producing the operating pressure with the aid of pumps, it is also possible to charge the reservoir kettle with compressed gas. For pressures of up to 15 bar, the throughput per individual jet is about 500 liters per hour, and is about 1,000 liters per hour at 60 bar. A further increase in the throughput can be achieved by increasing the number of jets and/or by connecting several jet dispersers in parallel.

EXAMPLE 1

Suntan milk

The organic phase (oily phase), consisting of: 200–400 kg of emulsifier, such as cetyl-stearyl alcohol and sodium cetyl-stearyl sulphate, and non-ionic emulsifiers, 1,200–1,600 kg of decyl oleate or liquid hydrocarbons, 0.5–2 kg of antioxidants, 50–200 kg of oilsoluble UV filter substance, such as methyl-phenylbenzoxazole, 5–20 kg of anti-foaming agent and 100–200 kg of perfume oil, is initially introduced in a normal stirred kettle 3 at 60° C., and the cold aqueous phase, consisting of: 300–800 kg of water and 100–300 kg of water-soluble UV filter substance, such as Novantisol-sodium, is added. Brief stirring gives an emulsion concentrate of the W/O type of about 40° C. This is homogenised under a pressure of 10 bar through the jet disperser 4 into the storage tank 5 containing 6,000–8,000 kg of water, 30–100 kg of buffer substance, such as disodium hydrogen phosphate, and 10–30 kg of preservative. Phase inversion takes place in the jet disperser 4. Whilst the mixture is passed in the storage tank 5, it is stirred. 10,000 kg of finished, liquid suntan emulsion of the O/W type with a very high degree of dispersivity are thus formed.

EXAMPLE 2

Vanishing cream of the O/W type

The organic phase (oily phase), consisting of: 150–300 kg of an emulsifier mixture of polyoxyethylene stearate and sorbitan fatty acid ester, 400–800 kg of cetyl-stearyl alcohol and 600–1,200 kg of octyldodecanol or liquid hydrocarbons, is melted at 70° C. in a normal kettle 2 and the melt is cooled to 40° C.

The oil-soluble active compounds and 20–40 kg of perfume oil are then added.

20–40 kg of a carboxyvinyl polymer are dispersed in 6,000–8,000 kg of water of 45° C. in another kettle 1, and 300–600 kg of 1,2-propylene glycol are added. After the mixture has been brought to 40° C., the water-soluble active compounds are added.

The aqueous phase is then added to the oily phase in stirred kettle 3, and 100–150 kg of 10% strength sodium hydroxide solution are added to neutralise the mixture.

After brief stirring, the still liquid emulsion is homogenised by the jet disperser 4 under a pressure of 10–15 bar. After homogenisation, the cream solidifies in storage tank 5. 10,000 kg of vanishing cream of the O/W type with a very high degree of dispersivity are thus formed.

EXAMPLE 3

Night cream of the W/O type

The oily phase of: 1,500–3,000 kg of ointment base consisting of mixtures such as: fatty acid esters and fatty alcohol esters (non-ionic) and mineral fats, 50–150 kg of aluminium tristearate, 200–400 kg of octyldodecanol, 50–150 kg of microcrystalline wax and 600–1,000 kg of hydrocarbons is melted in a normal kettle 2 at 80° C. and the melt is cooled to 75° C.

The aqueous phase, consisting of: 4,500–6,000 kg of demineralised water, 25–75 kg of magnesium sulphate, 200–400 kg of glycerol and 10–40 kg of preservative, is prepared in another kettle 1 and brought to 45° C.

The water-soluble active compounds are added to the aqueous phase.

The aqueous phase is then added to the oily phase in the stirred kettle, while stirring. After the crude emulsion has been cooled to 45°–50° C., the oil-soluble active compounds and 40–80 kg of perfume oil are added. A water-in-oil emulsion (W/O emulsion) is thereby formed. After the perfume oil has been incorporated, the still liquid W/O emulsion is homogenised in the jet disperser 4 under a pressure of 10–15 bar and is filled into the storage tank 5, where it solidifies to the finished cream. The W/O emulsion is thereby retained, that is to say no phase inversion takes place.

EXAMPLE 4

Preparation of ointment

The organic phase (oily phase), consisting of: 100–200 kg of octyldodecanol, 10–35 kg of sorbitan fatty acid esters or liquid paraffins, 20–45 kg of wax mixtures, 80–125 kg of cetyl-stearyl alcohol, 5–25 kg of preservative and 5–20 kg of one or more pharmaceutical active compounds (for example azole, imidazole or triazole derivatives), is melted at 50°–75° C. in a stirred melting kettle 3 and the melt is then cooled again to 35°–45° C. The aqueous phase consisting of: 550–750 kg of sterilised water with a temperature of 38°-45° C., is then emulsified into the oily phase (W/O emulsion). Pharmaceutical active compounds, emulsifiers and thickeners may also be added to the aqueous phase. The pre-emulsion thus prepared is then pumped through the jet disperser 4 under an initial pressure of 10-15 bar and with a substance flow of 1,000-2,000 kg per hour, and is thereby homogenised. The initial W/O emulsion is thereby inverted into the desired O/W emulsion (oil-in-water emulsion). The finished ointment can either be directly filled into tubes, or it can first be cooled in a storage tank 5. Alternatively, cooling can also be effected "in line" by means of a heat exchanger between the jet disperser 4 and the storage tank 5.

We claim:

1. Process for the preparation of fineparticled, stable, pharmaceutical or cosmetic dispersions consisting of an aqueous phase and an organic oily phase which is insoluble or not completely soluble in water, characterized in that a pre-emulsion is pumped through a jet disperser under a pressure of 2 to 50 bar, said jet disperser consisting of one or more jets, which are designed as capillary bores with a diameter of 0.5 to 0.8 mm and have a length to diameter ratio of 1.5 to 2 in the course of which all the pressure energy is consumed in the dispersing zone and the dispersion leaves the dispersing zone as a nondirectional stream.

2. A process according to claim 1, wherein the organic phase contains a mixture of glycerol esters or fatty acid esters and/or liquid, semi-solid and solid hydrocarbons, as well as polyhydric alcohols, non-ionic emulsifiers and fat-soluble pharmaceutical or cosmetic active compounds, and the aqueous phase contains an aqueous solution of glycerol, glycols, low-molecular monohydric alcohols and cosmetic or pharmaceutical active compounds, with the addition of substances which increase the viscosity and preservatives.

3. A process according to claim 1, wherein the pre-emulsion is pumped through the jet disperser under a pressure of 10 to 50 bar.

* * * * *